Figure 1:
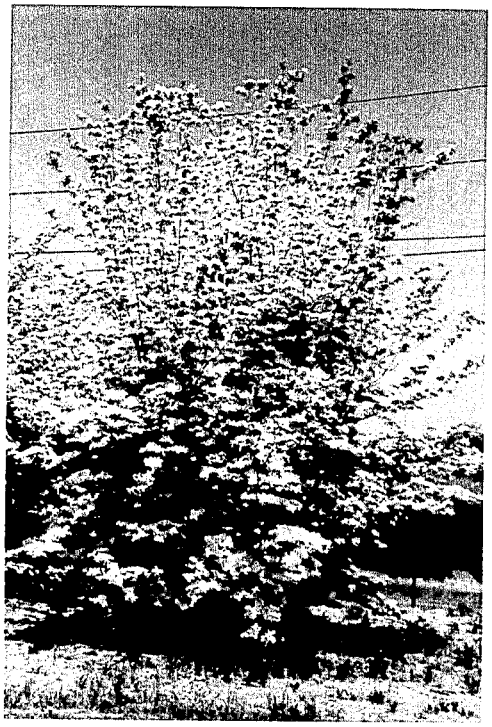

United States Patent [19]

Orton, Jr.

[11] Patent Number: Plant 7,210

[45] Date of Patent: Apr. 3, 1990

[54] DOGWOOD TREE 'CONSTELLATION'

[75] Inventor: Elwin R. Orton, Jr., Somerville, N.J.

[73] Assignee: Rutgers University, New Brunswick, N.J.

[21] Appl. No.: 262,687

[22] Filed: Oct. 26, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An interspecific hybrid of *C. kousa* and *C. florida*, being white-bracted and very floriferous, the floral display from May 17 to June 1 being intermediate to that of plants of *C. florida* and *C. kousa* and also exhibiting an upright habit typical of plants of *C. kousa* but more vigorous, the size at maturity usually being larger.

2 Drawing Sheets

BACKGROUND OF THE DISCLOSURE

This invention is the product of a long continuing program of interspecific hybridization of dogwood trees and more particularly of *Cornus florida* L. and *Cornus kousa* Hance and in fact of another, *Cornus nuttallii* Audubon which ultimately resulted in the selection of a number of $F_1$ interspecific hybrids (*C. kousa*×*C. florida*), which are believed to have attraction for distribution in commerce and for other purposes.

The hybrids of the general class to which this instant hybrid is directed, are notable because of their floral display, high vigor, and resistance to the dogwood borer.

Plants of *C. florida* are known to be among the most popular of the small flowering trees which are found in eastern and south central regions of the United States to which this species is indigenous.

As most people are clearly aware dogwood is often a spring flowering sort of tree or plant and yet the winter silhouette of the horizontal branches also makes them attractive both in cultivated and wild areas.

Unfortunately some of the problems which are the product of nature and weather in the areas where the plants have been grown and have been found, have caused some serious disease difficulties in known plants and as a result the instant cultivar of the hybrid program referred to is believed to offer a very attractive answer for those who wish to cultivate and grow dogwood trees for their attractive appearance.

SPECIFIC DETAILS OF THE INVENTION

The interspecific hybrid of *C. kousa* and *C. florida* to which this invention is directed has not been reported previously as far as is known. Thus this particular white-bracted hybrid is entirely new in commerce and is very floriferous. The floral display appearing as it does between May 17 and June 1 is intermediate to that of plants *C. florida* and *C. kousa*. The upright habit typical of the plants *C. kousa* being notable but more vigorous and the size at maturity is larger.

This particular cultivar to which the foregoing is applicable, has been asexually reproduced and found to retain its distinctive characteristics through successive generations, the name of this cultivar for use in commerce is 'Rutcan' and will be known by that title hereinafter.

It should also be noted that the floral bracts are of substantially large size and the diameter of the inflorescence as measured from tip to tip of the opposing outer bracts is relatively large, on the order of about 112 mm.

The average length of the inner bracts is approximately 61.5 mm and the average length of the outer bracts is approximately 55.0 mm.

In contrast when the floral bracts are fully expanded, the diameter of the inflorescence from tip to tip of the opposing inner bracts is about 125 mm.

The average width of the inner bracts at their widest point is approximately 35.8 mm; the average width of the outer bracts at their widest point is approximately 37.5 mm.

Other aspects and specific notations in respect to both color and size of this particular variety are disclosed in the appended detailed description of the new cultivar and in some cases additional description is enlarged upon to point out outstanding aspects.

As far as the reference to color is concerned, it is notable that the Royal Horticultural Colour Chart is availed of for specific designations where applicable.

It is probably desirable to indicate that the instant cultivar 'Rutcan' is contrasted with some of the other cultivars developed in this program and referred to by name herein by way of distinction as well as noting the respective differences of certain of them in this regard.

Specifically it should be noted that this cultivar is upright in habit as compared with the low, spreading form of one of its associated cultivars known as 'Stardust' (unpatented) and differs from other of its related cultivars which are upright growing plants known as 'Rutdan', 'Rutban', and 'Rutgan', (also unpatented) the floral bracts not being rounded and overlapping as in the foregoing referred to hybrids.

The number of true flowers per flower head is distinctly less in this particular cultivar (average=approximately 25.9) than in any of the foregoing named other hybrids.

Further the floral bracts provide a white floral display in the spring which is contrasted particularly to the floral bracts of 'Rutgan' which more tightly enclose the true flowers in the overwintering flower buds and provide a spring floral display of pink floral bracts.

The shape of the bracts is described as sessile, obovate with acute tips. The margins of adjacent bracts do not touch or overlap except at the point of basal attachment. The inner bracts are longer and narrower than the outer, or lower, bracts.

In the drawings:

FIG. 1. shows a tree of my new cultivar in bloom.

Figure 2:
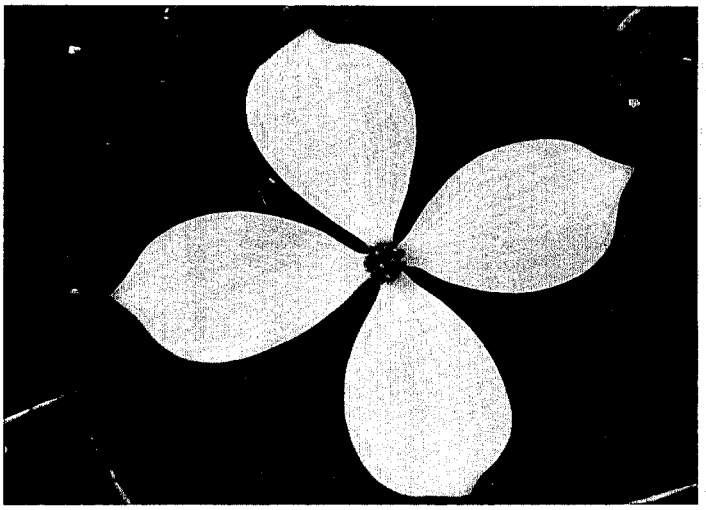

FIG. 2. shows four floral bracts with central subtended flower heads typical of my new cultivar.

SPECIFIC DESCRIPTION

Parentage:

*Seedling.*—Seed parent unnamed seedling of *Cornus kousa* Hance. Pollen parent *Cornus florida* L. cv. 'Cherokee Princess'.

Tree: When 17 years old—6.1 meters tall—5.6 meters spread, vigorous, upright, dense. Slightly vase-shaped when young, becoming densely upright with age, but highly sterile. Hardy, very floriferous annually.

*Trunk.*—Medium, smooth when young, but becoming shaggy with age, as then exhibits exfoliating bark.

*Branches.*—Medium, smooth, brown-gray. Lenticels — Numerous, medium.

*Leaves.*—Abundant. Length: 9.5–12.2 cm. (Average=11.0). Width: 4.4–6.5 cm. (Average=5.6). Medium, elliptic with acuminate tip; crenate to oblique base. Medium, dark green. Upper surface=RHS Colour Chart 139A. Lower surface=RHS Colour Chart 138B (Green Group). Margin—Crenate. Petiole—Short 8–15 mm. (average=10.6) Medium.

Flower buds: (The true flowers are small and numerous and are borne in flower heads. They are relatively inconspicuous. The floral display is provided by large floral bracts that subtend the flower heads. In common terminology and usually in the art, the floral bracts are described as though they were the flowers.) Hardy; in U.S.D.A. Plant Hardiness Zone 6a (−10 degrees F.). Medium size (larger than those of *C. kousa* but smaller than those of *C. florida;* plump; covered with light brown pubescence. Approximately 10–45% of the true flowers are naked, or visible, in the overwintering flower buds as the floral bracts do not overlap one another.

Floral bracts:

*Color.*—Start of floral display: Upper surface RHS 157 A (Green-white group). Lower surface RHS 157 C (Green-white group). Peak of floral display: Upper surface RHS 157 B (Green-white group). Lower surface Same as start and throughout.

I claim:

1. A new and distinct cultivar of Dogwood Tree, substantially as herein shown and described, characterized particularly as to novelty by the unique combination of its vigor and highly floriferous, small flowering form, similar to its seed parent *C. kousa* as to its upright, vase-shaped habit of growth but intermediate *C. Kousa* and its pollen parent *C. florida,* in the nature of the overwintering flower buds and the period of floral display, together with resistance to Dogwood Borer and Dogwood Decline.

* * * * *

UNITED STATES PATENT AND TRADEMARK OFFICE

CERTIFICATE OF CORRECTION

PATENT NO. : Plant 7,210

DATED : April 3, 1990

INVENTOR(S) : Orton, Jr.

It is certified that error appears in the above-identified patent and that said Letters Patent is hereby corrected as shown below:

On the title page, item [54], "'CONSTELLATION'" should be --'RUTCAN'--.

Signed and Sealed this

Twelfth Day of February, 1991

*Attest:*

HARRY F. MANBECK, JR.

*Attesting Officer*

*Commissioner of Patents and Trademarks*